(12) United States Patent
Pleschke et al.

(10) Patent No.: US 7,524,976 B2
(45) Date of Patent: *Apr. 28, 2009

(54) PROCESS FOR PREPARING DIFLUOROBENZO-1,3-DIOXOLE-5-CARBOXYLIC ACID DERIVATIVES

(75) Inventors: Axel Pleschke, Köln (DE); Albrecht Marhold, Leverkusen (DE)

(73) Assignee: LANXESS Deutschland GmbH, Leverkusen (DE)

( * ) Notice: Subject to any disclaimer, the term of this patent is extended or adjusted under 35 U.S.C. 154(b) by 561 days.

This patent is subject to a terminal disclaimer.

(21) Appl. No.: 11/127,403

(22) Filed: May 12, 2005

(65) Prior Publication Data

US 2005/0277692 A1    Dec. 15, 2005

(30) Foreign Application Priority Data

May 14, 2004    (DE) ................. 10 2004 024 010

(51) Int. Cl.
*C07D 317/44* (2006.01)
*C07D 317/00* (2006.01)

(52) U.S. Cl. .................. 549/434; 549/436; 549/437
(58) Field of Classification Search .......... 549/434, 549/436, 437
See application file for complete search history.

(56) References Cited

U.S. PATENT DOCUMENTS

| 2,688,026 | A | * | 8/1954 | Krimmel ................. 549/436 |
| 2,708,638 | A | * | 5/1955 | Broyles et al ............ 252/589 |
| 4,895,871 | A | * | 1/1990 | Lutomski et al. ......... 514/469 |
| 5,194,628 | A | * | 3/1993 | Ackermann et al. ....... 548/526 |
| 5,234,899 | A | * | 8/1993 | Knuppel et al. .......... 504/296 |
| 5,432,290 | A | * | 7/1995 | Casado et al. ........... 549/434 |
| 5,637,737 | A | * | 6/1997 | Andres et al. ........... 549/434 |
| 7,148,365 | B2 | * | 12/2006 | Pleschke .................. 549/534 |

FOREIGN PATENT DOCUMENTS

DE    100 38 019    2/2002

OTHER PUBLICATIONS

L. M. Yagunol'skii et al, Institute of Organic Chemistry, vol. 31, No. 2, Feb. 1961, pp. 628-632, "Cyanine Dyes Containing Fluorine IX. Cyanine Dyes From 5,6-(Difluoromethylene)-Dioxgenzthiazole Derivatives".

L. M. Yagupol'skii et al, Translated from Zhurnal Obshchei Khimii, vol. 30, No. 9, Sep. 1960, pp. 3129-3132, "Fluorine Content of Analogs of Anisaldehyde and Piperonal".

* cited by examiner

*Primary Examiner*—Janet L. Andres
*Assistant Examiner*—Raymond Covington
(74) *Attorney, Agent, or Firm*—Michael A. Miller

(57) ABSTRACT

The invention relates to a process for preparing difluorobenzo-1,3-dioxole-5-carboxylic acid and derivatives thereof, and to the use thereof for preparing medicaments and crop protection agents.

5 Claims, No Drawings

PROCESS FOR PREPARING DIFLUOROBENZO-1,3-DIOXOLE-5-CARBOXYLIC ACID DERIVATIVES

The invention relates to a process for preparing difluorobenzo-1,3-dioxole-5-carboxylic acid and derivatives thereof, and to the use thereof for preparing medicaments and crop protection agents.

Difluorobenzodioxole-5-carboxylic acid and derivatives thereof play an important role as precursors for active agrochemical and pharmaceutical ingredients, see also U.S. Pat. No. 4,895,871.

Two processes for preparing difluorobenzo-1,3-dioxole-5-carboxylic acid and derivatives thereof are known to date. For instance, U.S. Pat. No. 4,895,871 describes a two-stage synthetic sequence starting from difluorobenzo-1,3-dioxole, which provides for a bromination step and also a lithiation, quenching with carbon dioxide and aqueous acidic workup. Owing to the highly sensitive organolithium intermediates, this process is unpracticable for industrial use. In addition, Yagupolski, Troitskaya, Russ. J. Org. Chem., 30.9.1960, 3129-3132 disclosed the initial chlorination of benzodioxole-5-carboxylic acid with phosphorus pentachloride to give dichlorobenzodioxole-5-carbonyl chloride and the performance of the further reaction with antimony trifluoride to give difluorobenzo-1,3-dioxole-5-carbonyl fluoride. Owing to the high cost and the toxicity of antimony trifluoride, this process too cannot be used on the industrial scale.

There is thus a need for a process which enables the preparation of difluorobenzo-1,3-dioxole-5-carboxylic acid and derivatives thereof starting from readily available reactants, even on the industrial scale.

A process has now been found for preparing compounds of the formula (I)

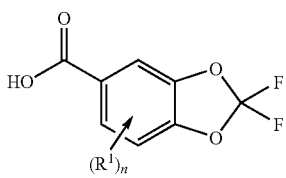

in which
R$^1$ is C$_1$-C$_{12}$-alkyl, C$_1$-C$_{12}$-fluoroalkyl, C$_1$-C$_{12}$-alkoxy, C$_1$-C$_{12}$-fluoroalkoxy, bromine, chlorine or fluorine and
n is 0, 1, 2 or 3, which is characterized in that compounds of the formula (II)

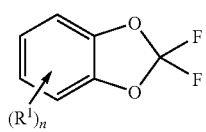

are reacted in the presence
of boron trifluoride and
hydrogen fluoride
initially to give compounds of the formula (III)

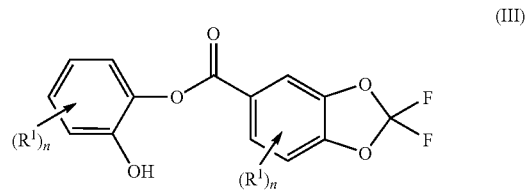

and the compounds of the formula (III), optionally after at least partial removal of boron trifluoride and/or hydrogen fluoride by distillation,
are hydrolysed in aqueous acidic or alkaline medium to give compounds of the formula (I).

The scope of the invention embraces all radical definitions, parameters and illustrations above and listed hereinbelow, in general or within areas of preference, in any combination with one another, i.e. also between the particular areas and areas of preference.

Alkyl and alkoxy are each independently a straight-chain, cyclic, branched or unbranched alkyl and alkoxy radical respectively, and the radicals mentioned may optionally be further substituted by C$_1$-C$_4$-alkoxy radicals.

C$_1$-C$_{12}$-Alkyl is, for example and with preference, methyl, ethyl, n-propyl, isopropyl, n-butyl, sec-butyl, tert-butyl, n-pentyl, 1-methylbutyl, 2-methylbutyl, 3-methylbutyl, neopentyl, 1-ethylpropyl, cyclohexyl, cyclopentyl, n-hexyl, n-heptyl, n-octyl, n-decyl and n-dodecyl.

C$_1$-C$_{12}$-Alkoxy is, for example and with preference, methoxy, ethoxy, n-propoxy, isopropoxy, n-butoxy, sec-butoxy, tert-butoxy, n-pentoxy, cyclohexoxy, cyclopentoxy, n-hexoxy, n-heptoxy, n-octoxy, n-decoxy and n-dodecoxy.

Fluoroalkyl and fluoroalkoxy are in each case independently a straight-chain, cyclic, branched or unbranched alkyl radical and alkoxy radical respectively, each of which is substituted singly, multiply or fully by fluorine atoms.

For example, C$_1$-C$_{12}$-fluoroalkyl is trifluoromethyl, 2,2,2-trifluoroethyl, pentafluoroethyl, nonafluorobutyl, heptafluoroisopropyl, perfluorooctyl and perfluorododecyl.

For example, C$_1$-C$_{12}$-fluoroalkoxy is trifluoromethoxy, 2,2,2-trifluoroethoxy, pentafluoroethoxy, nonafluorobutoxy, heptafluoroisopropoxy, perfluorooctoxy and perfluorododecoxy.

The preferred substitution patterns are defined hereinbelow:

R$^1$ is more preferably methyl, ethyl, n-propyl, chlorine, fluorine and bromine, most preferably chlorine or fluorine.

n is preferably 0, 1 or 2, more preferably 0 or 1 and most preferably 0.

Preferred compounds of the formula (II) are 2,2-difluorobenzo-1,3-dioxole, 2,2-difluoro-5-chlorobenzo-1,3-dioxole and 2,2-difluoro-5-bromobenzo-1,3-dioxole.

Preferred compounds of the formula (I) are 2,2-difluorobenzo-1,3-dioxole-5-carboxylic acid, 6-chloro-2,2-difluorobenzo-1,3-dioxole-5-carboxylic acid and 2,2-difluoro-(6-bromo-benzo-1,3-dioxole-5-carboxylic acid.

The compounds of the formula (III) have not been described to date and are therefore likewise embraced by the invention as indispensible intermediates. The definition including the areas of preference mentioned applies to $R^1$ and n in the same manner.

Preferred compounds of the formula (III) are 2-hydroxyphenyl 2,2-difluorobenzo-1,3-dioxole-5-carboxylate, 5-chloro-2-hydroxyphenyl 6-chloro-2,2-difluorobenzo-1,3-dioxole-5-carboxylate and 2-hydroxyphenyl 5-bromo-2,2-difluorobenzo-1,3-dioxole-5-carboxylate.

The process according to the invention is carried out in the presence of boron trifluoride and hydrogen fluoride. It is clear to those skilled in the art that the two components combine to give tetrafluoroboric acid, without this being mentioned specifically in each case.

The molar ratio of boron trifluoride to compounds of the formula (I) may, for example, be 0.1 to 10, but preferably 0.3 to 3 and more preferably 0.4 to 0.7. Larger amounts are possible but uneconomic.

The molar ratio of hydrogen fluoride to compounds of the formula (I) may, for example, be 0.1 to 100, but preferably 1 to 30 and more preferably 2 to 15. Larger amounts are possible but uneconomic.

The reaction temperature in the first step may, for example, be −30 to 100° C., preferably 0 to 50° C., and the reaction pressure 0.5 to 100 bar, preferably 0.9 to 12 bar.

The metering sequence between compound of the formula (I), boron trifluoride and hydrogen fluoride is arbitrary, but for reasons of practicability preference is given to admixing hydrogen fluoride with boron trifluoride and subsequently with compound of the formula (I), or to admixing compound of the formula (I) initially with hydrogen fluoride and then with boron trifluoride.

The compounds of the formula (III) which are formed in the first step, preferably after at least partial removal of boron trifluoride and/or hydrogen fluoride by distillation, are hydrolysed in aqueous acidic or alkaline medium to give compounds of the formula (I).

In this context, partial means preferably the removal by distillation of 60 to 98% of the excess boron trifluoride and/or hydrogen fluoride.

Preference is given to effecting the hydrolysis in aqueous alkaline medium, aqueous alkaline meaning, as is generally customary, a pH of above 7 at 25° C. For hydrolysis, it is possible to use, for example, alkali metal or alkaline earth metal hydroxides or carbonates, preferably alkali metal hydroxides, or in each case aqueous solutions thereof; particular preference is given to a 1 to 50% by weight aqueous solution of potassium hydroxide.

In the course of the alkaline hydrolysis, the phenoxides corresponding to the formula (III) are formed initially, and are likewise embraced by the invention, before the carboxylic acid salts of compounds of the formula (I) form.

To release the free carboxylic acids of the formula (I), preference is given to acidifying in the case of alkaline hydrolysis, specifically with an acid which has a pKa at 25° C. which is higher, preferably at least 2 units higher, than that of the acid to be released. For example, sulphuric acid optionally diluted with water may be used.

In the inventive manner, compounds of the formula (I) may be obtained in high purity and yield in a simple manner.

The invention further relates to a process for preparing compounds of the formula (IV)

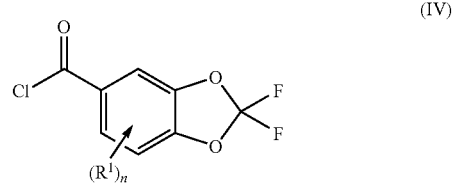

(IV)

in which
$R^1$ and n each have the definitions and areas of preference given above, which is characterized in that it comprises the process described above and, as a further step, the reaction with a chlorinating agent.

Suitable chlorinating agents are, for example and in particular, thionyl chloride, phosgene and phosphoryl chloride.

The inventive compounds of the formula (III) and the phenoxides thereof are especially suitable for use in a process for preparing medicaments, agrochemicals or intermediates thereof.

EXAMPLES

Example 1

2-Hydroxyphenyl 2,2-difluorobenzo-1,3-dioxole-5-carboxylate 880 ml of HF were initially charged at 0° C. and 259 g of $BF_3$ were injected within 30 min. Subsequently, 1000 g of difluorobenzodioxole were added within 30 min and 1 bar of nitrogen was injected. The temperature was raised to 15° C. within 30 min and the mixture was subsequently stirred at 15° C. for a further 10 hours.

The mixture was forced onto 1500 g of ice-water and the crystalline precipitate was dissolved by adding methylene chloride. The organic phase was removed and adjusted to pH ~5 with saturated sodium hydrogencarbonate solution. Again, the organic phase was removed, washed with water, dried and concentrated. 811 g of colourless solid were obtained ($\hat{=}$43.3% or 86.6% based on difluorobenzodioxole used).

$^1$H NMR (400 MHz, DMSO-$D_6$): 9.83 (b, 1H), 8.07 (m, 2H), 7.59 (m, 1H), 7.15 (m, 2H), 7.02 (m, 1H), 6.87 (m, 1H)

Example 2

2,2-Difluorobenzo-1,3-dioxole-5-carboxylic acid 1012 g of HF were initially charged at 0° C. and 257 g of $BF_3$ were injected within 60 min. Subsequently, 1000 g of difluorobenzodioxole were added within 60 minutes and the temperature was raised to 15° C. within 30 min. Subsequently, the mixture was stirred at 15° C. for a further 16 hours. Subsequently, 773 g of HF were distilled off at standard pressure up to internal temperature 55° C.

5 l of 10% KOH solution were initially charged and the residue of the distillation was added dropwise with cooling. On completion of addition, the mixture was stirred at 50° C. for a further 6 h, in the course of which the pH was kept between 10 and 11 by adding KOH. Subsequently, the mixture was cooled, the precipitate was filtered off with suction and the mother liquor was adjusted to pH 5 using sulphuric acid. After filtration with suction and drying, 529 g of beige solid were obtained. Yield: 40.7% =̂81.4% based on difluorobenzodioxole.

$^1$H NMR (400 MHz, DMSO-D$_6$): 13.52 (b, 1H), 7.87 (m, 2H), 7.53 (d, 1H)

Example 3

2-Hydroxyphenyl 6-chloro-2,2-difluorobenzo-1,3-dioxole-5-carboxylate 830 g of HF were initially charged at 0° C. and 211 g of BF$_3$ were injected within 30 min. Subsequently, 1000 g of 5-chlorodifluorbenzodioxole were added within 30 min and the temperature was raised to 15° C. within 30 min. Subsequently, the mixture was stirred at 15° C. for a further 10 hours.

The mixture was forced onto 1500 g of ice-water and the crystalline precipitate was dissolved by adding methylene chloride. The organic phase was removed and adjusted to pH ~5 using saturated sodium hydrogencarbonate solution. Again, the organic phase was removed, washed with water, dried and concentrated. 1122 g of colourless solid were obtained.

$^1$H NMR (400 MHz, DMSO-D$_6$): 10.32 (b, 1H), 8.16 (m, 1H), 7.9 (s, 1H), 7.22 (d, 1H), 7.02 (m, 1H), 6.92 (m, 1H)

Example 4

6-Chloro-2,2-difluorobenzo-1,3-dioxole-5-carboxylic acid 723 ml of HF were initially charged at 0° C. and 212 g of BF$_3$ were injected within 60 min. Subsequently, 1000 g of 5-chlorodifluorobenzodioxole were added within 60 minutes and the temperature was raised to 15° C. within 30 min. Subsequently, the mixture was stirred at 15° C. for a further 16 hours. Afterwards, HF was distilled off at standard pressure up to internal temperature 55° C.

5 l of 10% KOH solution were initially charged and the residue of the distillation was added dropwise with cooling. On completion of addition, the mixture was stirred at 50° C. for a further 6 hours, in the course of which the pH was kept between 10 and 11 by adding KOH. The mixture was cooled, the precipitate was filtered off with suction and the mother liquor was adjusted to pH 5 using sulphuric acid. After filtration with suction and drying, 466 g of slightly beige solid were obtained.

$^1$H NMR (400 MHz, DMSO-D$_6$): 13.52 (b, 1H), 7.68 (s, 1H), 7.65 (s, 1H)

What is claimed is:
1. Process for preparing compounds of the formula (I)

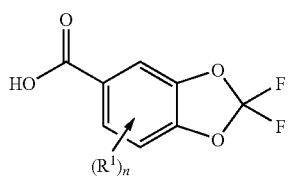

(I)

in which
R$^1$ is C$_1$-C$_{12}$-alkyl, C$_1$-C$_{12}$-fluoroalkyl, C$_1$-C$_{12}$-alkoxy, C$_1$-C$_{12}$-fluoroalkoxy, bromine, chlorine or fluorine and
n is 0, 1, 2 or 3,
characterized in that compounds of the formula (II)

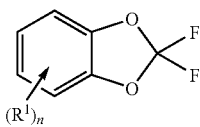

(II)

are reacted in the presence
of boron trifluoride and
hydrogen fluoride
initially to give compounds of the formula (III)

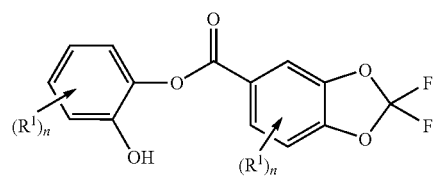

(III)

and the compounds of the formula (III), optionally after at least partial removal of boron trifluoride and/or hydrogen fluoride by distillation,
are hydrolysed in aqueous acidic or alkaline medium to give compounds of the formula (I).

2. Process according to claim 1, characterized in that R$^1$ is methyl, ethyl, n-propyl, chlorine, fluorine and bromine, and n is 0, 1 or 2.

3. Process according to claim 1, characterized in that the compounds of the formula (II) used are 2,2-difluorobenzo-1,3-dioxole, 2,2-difluoro-5-chlorobenzo-1,3-dioxole or 2,2-difluoro-5-bromobenzo-1,3-dioxole.

4. Compounds of the formula (III) and phenoxides thereof

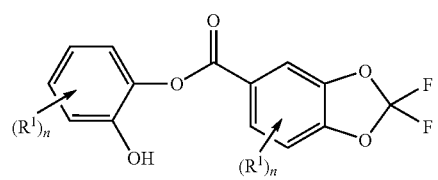

(III)

R$^1$ is C$_1$-C$_{12}$-alkyl, C$_1$-C$_{12}$-fluoroalkyl, C$_1$-C$_{12}$-alkoxy, C$_1$-C$_{12}$-fluoralkoxy, bromine, chlorine or florine and
n is 0, 1, 2 or 3.

5. The following compounds according to claim 4: 2-hydroxyphenyl 6-chloro-2,2-difluorobenzo-1,3-dioxole-5-carboxylate, 2-hydroxyphenyl 6-bromo-2,2-difluorobenzo-1,3-dioxole-5-carboxylate.

* * * * *